(12) United States Patent
Bonni

(10) Patent No.: US 7,608,067 B2
(45) Date of Patent: Oct. 27, 2009

(54) PATIENT-ADJUSTABLE INCONTINENCE DEVICE (AID)

(76) Inventor: Aram Bonni, 16012 Marguerite Pkwy., H-105, Mission Viejo, CA (US) 92602

( * ) Notice: Subject to any disclaimer, the term of this patent is extended or adjusted under 35 U.S.C. 154(b) by 900 days.

(21) Appl. No.: 10/703,287

(22) Filed: Nov. 6, 2003

(65) Prior Publication Data

US 2004/0147886 A1    Jul. 29, 2004

Related U.S. Application Data

(60) Provisional application No. 60/424,399, filed on Nov. 6, 2002.

(51) Int. Cl.
  A61F 5/44    (2006.01)
  A61M 1/00    (2006.01)
  A61F 2/02    (2006.01)
  A61F 2/04    (2006.01)

(52) U.S. Cl. ............ 604/323; 604/327; 604/540; 600/31; 623/23.66; 623/23.67; 623/23.68

(58) Field of Classification Search ............ 600/29–31, 600/40; 623/23.66, 23.67, 23.68; 604/317–326, 604/540–544
See application file for complete search history.

(56) References Cited

U.S. PATENT DOCUMENTS

| | | | | |
|---|---|---|---|---|
| 4,584,990 A | | 4/1986 | Haber et al. | |
| 4,881,530 A | * | 11/1989 | Trick | 600/40 |
| 4,917,110 A | * | 4/1990 | Trick | 600/40 |
| 5,030,199 A | | 7/1991 | Barwick et al. | |
| 5,067,485 A | * | 11/1991 | Cowen | 600/40 |
| 5,090,424 A | * | 2/1992 | Simon et al. | 128/885 |
| 5,101,813 A | * | 4/1992 | Trick | 600/40 |
| 5,562,689 A | | 10/1996 | Green et al. | |
| 5,964,806 A | | 10/1999 | Cook et al. | |
| 6,045,498 A | | 4/2000 | Burton et al. | |
| 6,102,848 A | * | 8/2000 | Porter | 600/29 |
| 6,319,191 B1 | | 11/2001 | Sayet et al. | |
| 6,475,137 B1 | * | 11/2002 | Elist | 600/40 |
| 2004/0002665 A1 | * | 1/2004 | Parihar et al. | 600/587 |

FOREIGN PATENT DOCUMENTS

WO    WO 97/41799    * 11/1997

OTHER PUBLICATIONS

American Medical Systems Manual "AMS 700™ Penile Prosthesis", Operating Room Manual, Dec. 2001, American Medical Systems, inc. Minnetonka, MN.

(Continued)

*Primary Examiner*—Tatyana Zalukaeva
*Assistant Examiner*—Ginger T Chapman
(74) *Attorney, Agent, or Firm*—Knobbe, Martens, Olson & Bear, LLP.

(57) ABSTRACT

A patient-adjustable device and surgical method for the treatment of urinary incontinence is disclosed herein. More specifically, the device is a mesh surrounded pillow which is implanted near the attachment of the urethra to the bladder, or mid to distal urethra which can be controlled by the patient. The fullness of the pillow can be controlled by the patient using two pressure-sensitive controls under the skin.

20 Claims, 8 Drawing Sheets

OTHER PUBLICATIONS

American Medical Systems Manual. "AMS Sphincter 800™ Urinary Control System", Operating Room Manual Oct. 2001, American Medical Systems, inc. Minnetonka, MN.

American Medical Systems, Brochure, Patient Information and use Instructions for the AMS 700™ Penile Prosthesis Product Line, 1999 American Medical Systems, Inc., Minnetonka, MN.

Bezerra CA. And Bruschini H, "Suburethral sling operations for urinary incontinence in women (Cochrane Review)", The Cochrane Library, Issue 1, 2002, Abstract.

Glazener CMA. And Cooper K., "Anterior vaginal repair for urinary incontinence in women (Cochrane Review)", The Cochrane Library, Issue 1, 2002, Abstract.

Gynecare Brochure, "Gynecare TVT with abdominal guides" Feb. 2002, Gynacecare Worldwide, a division of Ethicon a Johnson & Johnson company, Somerville NJ.

Herbison et al., "Weighted vaginal cones for urinary incontinence (Cochrane Review)", The Cochrane Library, Issue 1, 2002, Abstract.

Liapis et al., "Comparison of open retropubic colposuspension with tension-free vaginal tape for the treatment of genuine stress incontinence in women" $2^{nd}$ Department of Obstretics and Gynecology, Aretaieio Hospital, University of Athens, Greece, IC 2000 Tampere.

Moeherer et al., "Laparoscopic colposuspension for urinary incontinence in women (Cochrane Review)", The Cochrane Library, Issue 1, 2002, Abstract.

* cited by examiner

PATIENT-ADJUSTABLE INCONTINENCE DEVICE (AID)

This patent application claims priority under 35 U.S.C.§119 of U.S. Provisional application 60/424,399, filed Nov. 6, 2002, herein incorporated by reference in its entirety.

FIELD OF THE INVENTION

The invention relates to a patient-adjustable incontinence device (AID) and surgical method for the treatment of urinary incontinence. More specifically, the AID is a pillow which is implanted such that it aids in continence and can be controlled by the patient.

BACKGROUND OF THE INVENTION

Studies show that bladder control problems, also called urinary incontinence (UI), affect up to 30 percent of women over 60 and 18% of men, affecting more than 13 million U.S. adults. In addition, 25% of women ages 30-59 have experienced an episode of urinary incontinence. Urinary incontinence is the medical term used to describe the condition whereby one cannot control the flow of urine from one's body. This can result in involuntary loss of urine that can be demonstrated objectively and which constitutes a medical, social or hygienic problem. Urinary incontinence can be caused by a number of problems, including: mixed incontinence (used to describe patients, mainly women, who suffer from symptoms of both urge and stress incontinence), overactive bladder (involuntary contractions of the detrusor muscle of the bladder), sphincter abnormalities (stress incontinence—the involuntary loss of urine at a sudden increase in the abdominal pressure that occurs when the pressure within the bladder exceeds the maximum closure pressure of the urethra in the absence of activity of the detrusor muscle), and urge incontinence (associated with a sensation of urgency). Bladder control problems should never be accepted as a normal part of aging. Though it is readily diagnosed, most people do not discuss the symptoms of Urinary incontinence with their physicians. This is partly out of embarrassment or believing that it is a normal part of child bearing or aging, thus, many patients may not get treatment. Those that do, may not experience a cure, but may be too embarrassed to return or may decide to live with the discomfort rather than to try a further treatment.

Urinary incontinence is often described as loss of bladder control. However, it is not the bladder which is controlling the flow of urine. The bladder functions to collect and store urine. A circular muscle called the sphincter actually controls the flow of urine out of the bladder. Urinary incontinence usually happens because of many different factors, most of which are still unknown. But, it is believed that the end result is an increase in intravesical pressure that exceeds that of the urethral pressure and causes involuntary loss of urine. One cause may be a damaged sphincter which cannot squeeze and close off the urethra. In men, the sphincter is located below and above the prostate, and the prostatic smooth muscle is also intertwined with the whole sphincter mechanism. Another cause may be a damaged sphincter which cannot squeeze and close off the urethra.

Many of the methods used to surgically treat urinary incontinence rely on implanting a device into the tissue to restrict or constrict the urethra of the patient to maintain continence. Typically, the placement of the device will decide the level of continence after surgery. However, these devices/grafts are prone to being under- or over-inflated/stretched at the time of implant, leading to undesirable postoperative results. For example, if the devices/grafts are over-inflated/stretched and cause the urethra to be restricted too tightly, the patient is at risk for retention, a condition where the patient cannot pass urine. Such a condition could lead to kidney damage, necessitating major corrective surgery or at minimum use of self-catheterization to empty the bladder on a regular basis thus increasing the risk of urinary tract infection. Excessive occlusive forces are known to undesirably minimize arteriovascular blood flow to the urethra and thereby increase the possibility of ischemia and erosion to the delicate tissues.

Alternatively, if the devices/grafts are under-inflated/stretched or in some other way cause the urethra to be restricted too loosely, the patient still suffers from urinary incontinence. In addition, many of the previous devices and methods allow for a small amount of leakage. However, once the surgery is completed, there is no readily available means without additional surgery to accurately and continuously adjust the occlusive pressures which are applied to the urethra, or other lumen by the device or method, to achieve continence, or the correct amount of pressure.

More particularly, because of the swollen and aggravated condition of edema of the urethral tissues during and for a period subsequent to surgery, the physician cannot be certain as to the normalized condition of the patient's urethra until post-operative edema has subsided. Therefore, the physician must estimate the required minimal occlusive force needed to achieve continence. There is no data available in the literature to this date as to what degree these occlusive pressures should be at any given time. Thus, as a consequence of the need to estimate, sphincteric mechanisms and other devices are often improperly fitted or selected. Moreover, where conventional mechanisms include occlusive force control means, such force control is usually accomplished in large, step-wise increments. Therefore no artificial sphincters are known which are adapted to easily and accurately control or continuously vary the occlusive pressures needed to achieve continence, so that the sphincter may be percutaneously tailored to the individual needs of the patient on an ongoing basis without requiring additional surgery. In particular, no methods are available which can be controlled by the patient.

Thus, a method for the surgical treatment of Urinary Incontinence is needed which is simple, adjustable over time or as healing occurs, and results in a higher patient satisfaction. Preferably, the method of insertion is also less invasive and could eventually become an office procedure.

SUMMARY OF THE INVENTION

In accordance with the present invention, a patient-adjustable urinary incontinence device (AID) is provided. The AID can include a pillow, a reservoir in fluid communication with the pillow, and two control elements. The pillow and reservoir can be in fluid communication via tubing. The tubing also can include the control elements which allow the addition and removal of liquid or gas from the pillow and the reservoir. The control elements can be physically accessible to the patient. Alternatively, the control elements can be accessible via a remote control device. In some embodiments, there is also a valve which allows for the addition and removal of the liquid or gas from the urinary continence device. In one embodiment, the control elements are check valves. In a further embodiment, the control elements are a series of check valves. In one embodiment, the check valves are duckbill valves. In one embodiment, the pillow is manufactured of a resilient material. In a further embodiment, the reservoir is manufactured of a non-resilient material. In a further embodiment, the control elements are activatable by radiowaves, soundwaves, touch, pressure, and/or temperature. In a further embodiment, the control elements are activatable by remote control.

In accordance with another preferred embodiment of the present invention, a method of controlling urinary incontinence is provided. The method comprises providing a device comprising a pillow, reservoir, and a control element, wherein the pillow is located near the urethra, and adjusting the pressure applied by the pillow to the urethra by activating the control element. The control element can be just under the skin. In one embodiment, the control element comprises a bulb. In another embodiment, the control element comprises a pump. The control element may comprise a valve or a series of valves. The control elements can be activatable by radiowaves, soundwaves, touch, pressure, or temperature. Further, the control elements can be activatable via a remote control device. In a further embodiment, a remote control device is included which allows the patient to inflate or deflate as needed.

In accordance with another preferred embodiment of the present invention, a patient-adjustable urinary incontinence device is provided. The device can include a pillow, a patient-adjustable valve for draining the pillow; and a patient-adjustable pump for filling the pillow.

DETAILED DESCRIPTION OF THE PREFERRED EMBODIMENT

Figure 1:
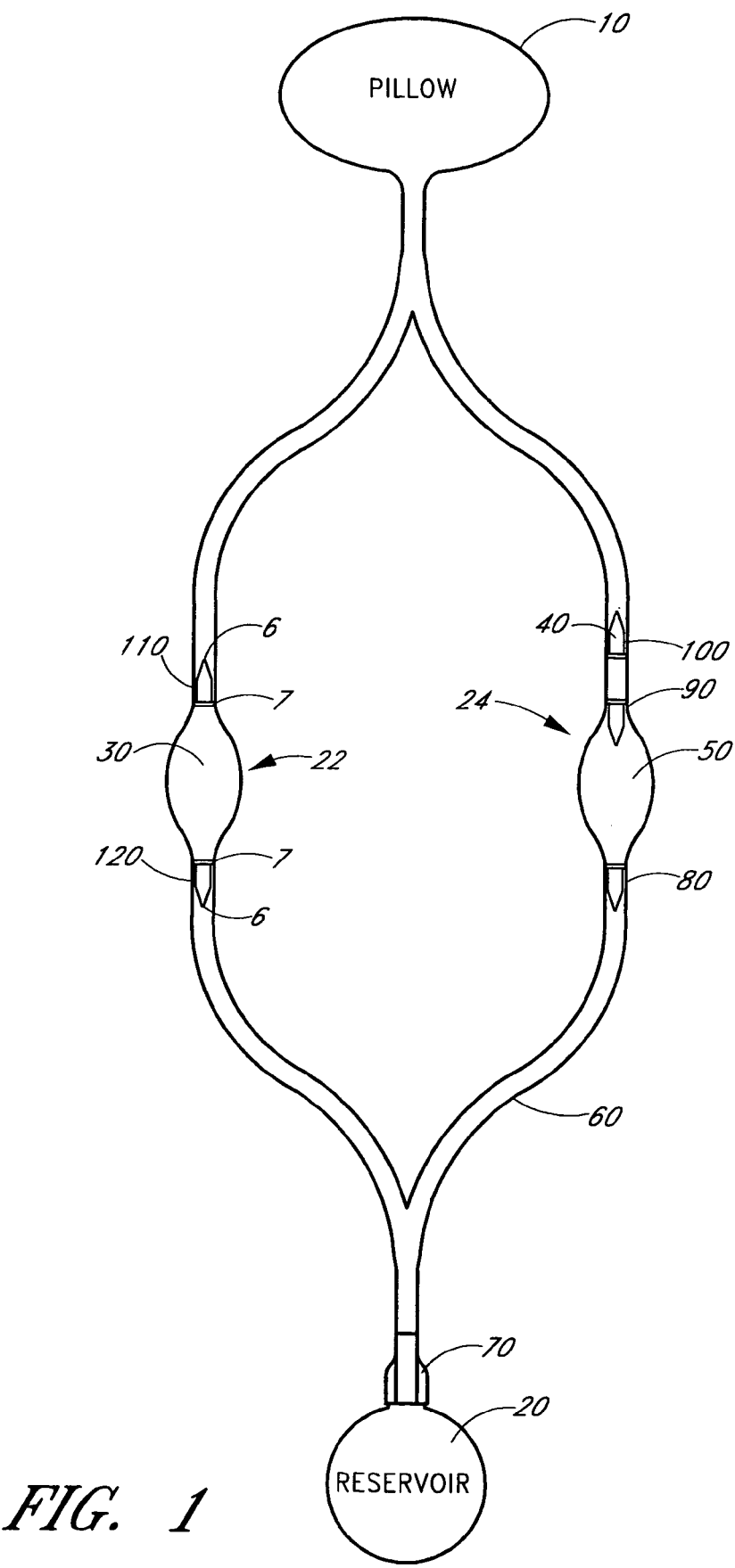
FIG. 1 is a front view of a urinary incontinence device of a preferred embodiment (the AID).
Figure 2A:
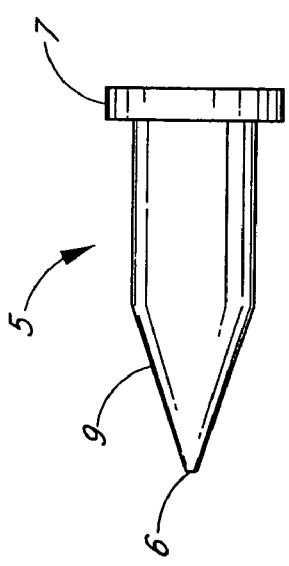
FIGS. 2A-F are views of a duckbill valve of preferred embodiments.
Figure 2B:
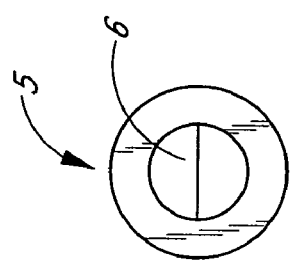
Figure 2C:
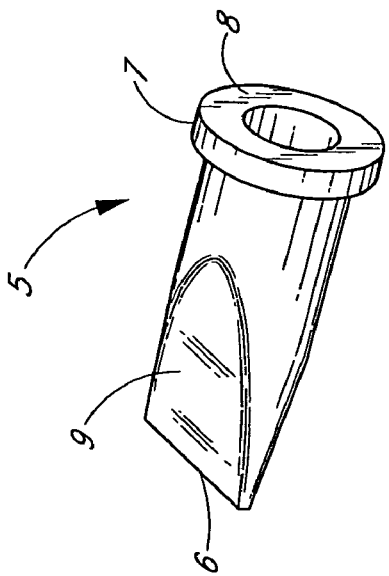
Figure 2D:
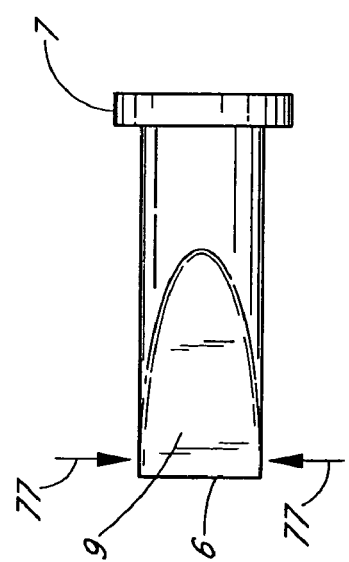
Figure 2E:
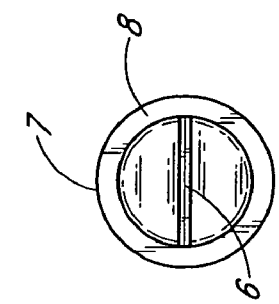
Figure 2F:
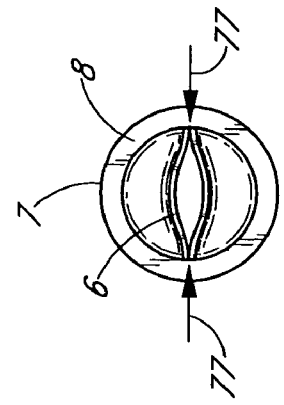

A patient-adjustable device and surgical method for the treatment of urinary incontinence is disclosed herein. More specifically, the device includes a pillow which is implanted near the attachment of the urethra to the bladder. The pillow may be inflated or deflated by the patient as needed and can be adjusted as needed due to post-operative changes, changes during healing, changes during aging, and even changes due to lifestyle without surgery or any invasive techniques. In one embodiment, the fullness of the pillow can be controlled by the patient using two pressure-sensitive control elements under the skin.

The surgical methods for correction of genuine stress incontinence have traditionally relied on some sort of bladder neck support and/or elevation. This could be achieved with or without the use of a synthetic graft through the vagina, by laparotomy, or more recently laparoscopically. More than 200 different types of procedures with different names have been identified which rely on the aforementioned basic goals of bladder neck elevation and support. More recently, the tension-free vaginal tape procedure provides mid to distal urethral support but uses a special vaginal tape which allows for ingrowth of collagen and tissue through the TVT (tape). During the procedure, the doctor checks for the correct amount of tension by asking the patient to cough. If more than a few drops of urine escape, the doctor tightens the tape. The method of measurement is very crude and can result in an over or under tightening of the tape which can only be repaired by further surgery. The use of local anesthesia has been suggested to allow the doctor to adjust the tape intraoperatively by talking to the patient, providing a better estimate of the tightness. However, in reality, this is not religiously adhered to in the U.S mostly due to widespread use of general anesthesia, which precludes talking to the patient during surgery. In addition, this procedure should not be performed on patients who are in the process of growing and women who may still wish to become pregnant. This is because the TVT will not stretch.

The problem that these and other previous procedures share is that once the bladder, bladder neck, or urethra has been positioned, it cannot be altered or adjusted. After surgery, as the tissues heal and the inflammation recedes, the positioning may have been slightly off, either overdone or underdone, such that the patient either has trouble urinating or still has incontinence. The patient has the choice to live with it as it is or to go through a second surgery. At this point it is often too embarrassing to return to the physician or the idea of a further surgery is unpleasant and unwanted.

In view of this problem, the method herein allows the surgeon to implant a device which can be adjusted as needed for any reason, including post-operative changes, changes during healing, changes during aging, and even changes due to lifestyle. Thus, the method and apparatus herein allows the surgeon to produce a cure without the need for further surgery.

The implantable medical device involves an inflatable pillow which can be positioned in such a way that it aids the patient with achieving continence. The implantable device may be manufactured of any material appropriate for biological use, which is biocompatible, does not cause any immune reaction and will last for a significant period of time in the body. The material can include, but is not limited to: biocompatible plastics of all kinds, silicones, and prolene strips.

The implantable medical device has the advantage of being adjustable both at the time of implantation and postoperatively. This postoperative adjustability of the implantable medical device allows the physician and/or patient to regulate the amount of pressure applied to the urethra to ensure continence of the patient and to minimize iatrogenic effects.

In one embodiment, a patient's incontinence is treated by positioning one or more of the implantable devices adjacent to at least one side of a patient's urethra so as to adjust liquid flow resistance in the urethra. This is accomplished by using the implantable device to coapt the patient's urethra so as to maintain a transverse cleft or slit structure of the collapsed urethra and thereby provide sufficient flow resistance to ensure continence, while still allowing the patient to consciously discharge urine when necessary. Thus, the patient does not have to activate the device each time he or she wants to urinate. However, the device may be adjusted to allow for normal urination if or when the initial adjustment is imperfect.

In one embodiment, the device is intended to work immediately adjacent to the urethral wall of a patient to create an increase in urethral coaptation and flow resistance. However, in the prior art devices any tissue change which occurred postoperatively, such as a reduction in tissue edema associated with the procedure, caused a reduction in clinical effect because of the reduced coaptation and resistance after the swelling had subsided. Although some minor degree of adjustability is available at the time of implantation in the prior art devices, they fall short in adjustability of the devices for the most important time, i.e. the postoperative period, in which the failure or overcorrection of the device is diagnosed. The present method and device make it possible to access the implanted device and adjust the inflation after implantation in a nonoperative manner and may be continually adjusted as needed during the life of the patient, or the endurance of the apparatus. In particular, the present method and device make it possible for the patient to make the adjustments and identify a comfortable level of inflation.

In one embodiment, the post implantation, or postoperative, urethral restriction is realized by the adjustable device acting on tissue adjacent to the walls of the urethral lumen and forcefully closing the urethral lumen. Voiding of urine from the bladder only occurs when the intravesicular pressure overcomes the resistance established by the adjustable device. In other words, an angle is maintained such that the patient must push the urine past an obstruction. The device, then, should require little adjustment except from about 1-2 times per year to about 1-2 times per the life of the patient.

The implantable medical device includes a reservoir, an inflatable pillow, and two control sites, one which allows the patient to inflate the pillow and the other which allows the patient to deflate the pillow. In an alternative embodiment, a single control site may suffice. The device may also include an activation valve which keeps fluid from inadvertently leaking from the pillow to the reservoir.

The reservoir may be any type of material which can be filled with a substance such as gas or liquid without leakage into the surrounding tissues or cavity. In one embodiment, the reservoir is manufactured of a material which is not extremely resilient, and has a limp appearance unless filled with liquid or a gas. This ensures that the reservoir will not be actively "pulling" the fluid into it. Thus, the reservoir may be any material known to one of skill in the art, including but not limited to biocompatible plastics and silicones.

In one embodiment, the reservoir is constructed to be able to hold an amount of liquid sufficient to allow for inflation and deflation of the pillow in an amount that the patient can adjust from about 0.1 mm to 30 mm, including from about 0.2 mm to about 10 mm, including 0.3 mm, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.5, 2.75, 3, 3.2, 3.5, 3.7, 4.0, 4.5, 5, 5.5, 6, 6.5, 7, 7.5, 8, 8:5, 9, and 9.5 mm. In a further embodiment, the pillow may be able to hold from about 1 to 300 cc, including 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, and 300.

In one embodiment, at least one pillow is used to constrict the urethra and\or bladder when inflated without leaking into the tissues or body cavity. The pillow may be any shape which allows it to more conveniently fit within the body without affecting other organs or tissues, including but not limited to: round, oval, kidney-shaped, square, rectangular, parallelogram, amorphous, rod-shaped. In one embodiment, the pillow is manufactured of the same material as the reservoir. However, in some embodiments, the pillow is manufactured of a material which has more resilience then that of the reservoir. In one embodiment, the resilience allows the pillow to revert to its normal shape. In a further embodiment, the resilience allows for fluid to be pulled into the pillow when there is little or no resistance from outside the pillow. In a further embodiment, the material may be stretched to inflate. In a further embodiment, the material and the pillow produce a pressure which pulls fluid into the pillow. Examples of materials which may be used to produce the pillow include but are not limited to silicone elastomers and equivalents.

In one embodiment, the pillow is implanted at any position in conjunction to the bulbous urethra. In a further embodiment, the pillow is implanted at any position in conjunction to the bladder neck. In a further embodiment, the pillow is implanted at any position in conjunction to the bladder. For a female, it is envisioned that the most useful position is at the urethra or bladder neck. For a male, it is envisioned that the most useful position is through a perineal approach to bulbous urethra. However, one of skill in the art knows that each body is different and the best positioning may have to be decided by the surgeon during the procedure.

In one embodiment, either the pillow and/or the reservoir may also include a mesh which allows the tissue and blood vessels to grow in and around the pillow and/or bladder. Such materials include, for example, but are not limited to: PROLENE mesh, or polypropylene material used in ETHICON sutures. The porous structure of such mesh allows for rapid tissue ingrowth, very low likelihood of urethral erosion as compared with other synthetic materials, and no foreign body reaction after implantation.

The reservoir and pillow may be filled with any material which may be moveable, such as a gas or liquid. Examples of liquids which may be used include, but are not restricted to: water, saline, buffered solutions, gels, silicone, a silicone lubricating fluid, Iothalamate solution or any other low compressibility material. The gas used can be any biocompatible gas including, but not limited to: air, oxygen, nitrous oxide, and mixtures of biocompatible gases. In one embodiment, the pillow and reservoir are filled with the same material. In a further embodiment, the pillow and reservoir are discontinuous (due to a filter or membrane) and contain different materials.

In one embodiment, the incontinence device contains a device or method to control movement of the material. Methods to control the influx and eflux of material into and out of the pillow may be any methods known to one of skill in the art. For example, in one embodiment, at least one one-way valve, duckbill valve or check valve is used. These valves typically allow the movement of material in only one direction with little or no leakage in the reverse direction. In one embodiment, one valve is used to control inflation of the pillow. In a further embodiment, at least two valves are used to control inflation. In a further embodiment, at least two valves are used to control deflation. In a further embodiment, the method to control inflation is different from the method to control deflation of the pillow. In a further embodiment, the resilience of the pillow may be used to activate or control the inflation of the pillow.

The control elements or adjustment devices used by the patient may be activated by any method known to one of skill in the art. Examples of such methods include, but are not limited to: radiowaves, sound, touch, pressure, or temperature (hot or cold). Non-patient activated methods may also be included, such as osmosis. In a further embodiment, a pump device may be used much like that used for penile prostheses such as the AMS 700™. This would allow the patient to pump enough fluid into the pillow from the reservoir or remove the fluid as needed.

In a further embodiment, a remote control device is connected to the AID such that the patient and/or physician can adjust the inflation and deflation by manipulating a hand-held or separate control mechanism. For example, a chip or other device may be inserted under the skin in enough proximity to the AID to be able to exert influence on it. The chip may be recognized by a remote device which the patient or physician can manipulate to make adjustments or to control the inflation and/or deflation of the AID. It is envisioned that any know remote control system may be used which is known to one of skill in the art. Further the device may be manipulated by the patient using a hand-held device, a device attached to a wristband, a device insertable or activatable by computer, a device which can fit into a purse or wallet, or any other system known to one of skill in the art. In one embodiment, the remote is a radio frequency remote, similar to those used with garage door openers. The receiver in the A/D (within the patient's body) receives control signals from the remote controller and activates a pump to turn on, or a valve to open. Other embodiments of the remote control device are set out herein.

In accordance with another preferred embodiment, a remote control patient-adjustable urinary incontinence device is provided. The incontinence device works to help the normal sphincter muscles to close, however, in some embodiments, the device may work with simple occlusion of the urethra. In its broadest use, the remote control is envisioned to open and, or shut down the urethral output, hence giving the patient an adjustable mode of controlling the bladder.

The remote control device can include a pillow, or a small platform that would cause occlusion of the urethra. When configured to use a pillow, one embodiment includes a patient-adjustable battery micro pump for draining and filling the pillow, a receiver for receiving signals and a transmitter for sending signals to the receiver in the battery pump. It is envisioned that, in its simplest form a signal from the transmitter will activate the battery micro pump to pump fluid from the reservoir into the pillow. In a further embodiment, a second signal from the transmitter may activate the same micro pump or a second micro pump to pump fluid from the pillow back into the reservoir. It is envisioned that the fluid can be pumped slowly so as to allow the patient to achieve a comfort level which may necessarily need very small changes in fluid level.

In a further embodiment, the remote control can operate a hydraulic or mechanical valve that would elevate an already full balloon or would fill the implanted platform or balloon to obstruct the urine flow. In some embodiments, the platform is a fluid filled balloon, however, alternatives can include anything known to one of skill in the art, including but not limited to an air-filled balloon, a soft platform which will not damage the tissue, a rounded platform, a vise-type mechanism (round or square), and a pillow surrounding the urethra.

In other embodiments, a level of fluid which keeps the urethra closed can be chosen so that when the system is in rest phase, the urethra is closed. The pump can then be activated to allow removal of the contents of the bladder until empty, and then stopped. When stopped, the system can then be allowed to go back to the rest phase with the urethra closed.

In a further embodiment, the default in case of break down is the open mode to restore an open urethral flow. This safety mechanism can be used with any of the embodiments described herein. In a further embodiment, physical adjustment devices are included which allow the patient to open the urethral flow at any time, whether because of break-down of a pump, a valve, or the remote device.

It is envisioned that when a physical adjustment is desired, the adjustment device or devices may be positioned under the skin in a region of the body which is not easily bumped, but still allows for ease of discrete accessibility. In one embodiment, the adjustment devices may be positioned in the soft tissue of the pelvic area. The pelvic area allows for ease of discrete accessibility, but enough protection that the adjustment devices may not be easily activated without the patient's knowledge. Alternatively, in a further embodiment the adjustment device may be located in any area including but not limited to: the abdominal area, the lower pelvis, the inner thigh, a position close to, but beneath the hip bone, the scrotum, the gluteus maximus, and the labia majoris and/or minoris of the vulvavaginal area in women.

It is envisioned that a site is chosen such that one could not easily inadvertently adjust or activate the device. In addition, it is envisioned that in order to activate the valves or the activation device, a method is used which would additionally ensure only purposeful activation. For example, any method may be used including, for example, but not limited to: constant heavy pressure, pinching, multiple pushes, pushing until a monitoring device is activated (such as a sound device), pushing for a minimum amount of pressure or time. In a further embodiment, activation requires a monitoring device to be activated, such as an audible or palpable device.

In a further embodiment, the inflation control element, deflation control element, and activation switch are separated from or different enough from each other such that the patient can be sure how to control the device. For example, the activation device might be a wider "button", the inflation device might be on the left and the deflation on the right, or vice versa. Alternatively, one may require heavy pressure, while the other requires multiple pushes.

In one embodiment, the activation valve keeps fluid from leaking back into the reservoir from the pillow. The activation valve may be any type of control known to one of skill in the art. However, in one embodiment, the activation valve is a duckbill or one-way valve which is positioned opposite the deflation valves and between the deflation valves and the pillow. The activation valve may be opened by pushing the duckbill valve in a direction toward the duckbill such that it is opened by the pressure. The duckbill valve may also include a button or a platform which would allow the user to identify where to push to open the valve.

In a further embodiment, the device may have a control mechanism that shuts off its functionality if more than 10 to 50 cc of the medium used has leaked into the surrounding tissues. This would alarm the patient and/or physician to a malfunction.

The material may flow from the pillow to the reservoir by any method known to one of skill in the art. In one embodiment, any tubing known to one of skill in the art may be used, including but not limited to: kink resistant tubing or biocompatible tubing. The same type of tubing may be used in both directions, from the pillow to the reservoir and from the reservoir to the pillow. In a further embodiment, a different type of tubing is used from the pillow to the reservoir than from the reservoir to the pillow.

In one embodiment, the pillow reservoir and tubing are produced to contain no breaks or openings which might allow contamination or infection. In a further embodiment, the implantable device is produced to be put together by the surgeon prior to operating while still maintaining a sterile internal space. For example, a seal may be broken which allows attachment of the reservoir to the tubing. The attachment may be any attachment known to one of skill in the art, including but not limited to: a luer lock, a screw lock, a ball and joint lock, an adhesive substance, or a materials attachment. It is envisioned that a materials attachment may involve the attachment made by two materials chosen such that they naturally adhere to each other.

In a further embodiment, the device may contain a sterile valve which allows for the introduction of a gas or liquid. The valve may be a one-way or two-way valve which allows for the addition or removal of liquid or gas as needed. Alternatively, the valve may be a rubber stopper which allows for the insertion of a syringe needle to insert or remove liquid or gas.

System

With reference to FIG. 1, the urinary incontinence device of a first preferred embodiment includes a pillow 10 and a reservoir 20 in fluid communication. The pillow 10 and reservoir 20 are connected by tubing 60. The tubing 60 is shown branching off to form two separate paths: an inflation path and a deflation path. The left side of the diagram provides the inflation path, while the right side of the diagram forms the deflation path. It is envisioned that the inflation and deflation paths may be reversed.

In this embodiment, two control elements 22 and 24 are provided between the pillow 10 and reservoir 20. The control elements 22 and 24 are located in the tubing 60 and allow for inflation and deflation, respectively. Control element 22 comprises a self-expanding inflation bulb pump 30 to control inflation of the pillow, while control element 24 comprises a self-expanding inflation bulb pump 50 to control deflation of the pillow.

In one embodiment, the control elements comprise check valves, positioned in the fluid flow path permitting flow in only one direction. For example, one or a series of check valves may be positioned on one part of the device such that fluid may only flow from the pillow to the reservoir. Similarly, one of more check valves may be positioned on the other side of the device such that fluid may only flow from the reservoir to the pillow. This allows the patient or doctor to add or remove liquid from the pillow as needed for comfort and control.

In the embodiment shown in FIG. 1, the control elements 22, 24 include a series of valves 80, 90, 100, 110, and 120. For example, the inflation control element 22 comprises two valves 110 and 120. The valves 110 and 120 are aligned directionally from the reservoir 20 to the pillow 10, such that liquid may flow from the reservoir 20 to the pillow 10, but not in reverse. In this embodiment, the inflation control pump 22 comprises a bulb 30 which is sensitive to pressure and, when pushed, forces liquid to flow from the reservoir 20 into the pillow 10.

With reference to FIG. 2, the duckbill valves 80, 90, 100, 110, 120 will be described. These valves may all be identical and are labeled 5 in FIG. 2. In FIGS. 2A-2E the duckbill valve 5 is shown closed, which occurs when fluid is not flowing through it, for example, when the patient has filled the pillow enough to achieve both comfort and continence. However, this would also be the appearance during backflow, for example when fluid tries to flow backward from the pillow to the reservoir, holding the fluid level to that chosen by the doctor and patient. FIGS. 2A-F show the generally V-shaped duckbill valve 5. The duckbill valve 5 has a rim 7, an opening 6, and two planar sides or ramps 9 which taper down to the opening 6. The opening 6 is produced by the convergence of the two ramps 9. When liquid or gas is flowing through the duckbill valve 5 the liquid flows in the direction from the rim 7 to the opening 6 and the opening is pushed open (see FIG. 2F). When the flow is stopped, the opening 6 returns to its static state, closed (see FIG. 2E). When a change in pressure causes a backflow of the liquid or a directional change of the liquid from the opening 6 to the rim 7, the opening 6 remains closed and no liquid is allowed to flow backwards. Without being restricted to the following theory, the shape of the duckbill valve 5 as well as the material memory keeps liquid which is flowing backwards from opening the seal formed by the opening 6. The water or liquid exerts pressure on the planar sides or ramps 9 which keeps the opening 6 closed. Alternatively, as shown in FIG. 2F, by applying pressure to the duckbill valve at approximately the point numbered as 77, the patient or surgeon can purposefully open the valve opening 6.

In order for fluid to flow from the pillow 10 to the reservoir 20, the activation valve 40 must be opened. This valve 100 is opened by pushing on the valve 100 so that it opens in a direction (see arrows 77 in FIG. 2C) such that the opening 6 is open, thus, allowing liquid to flow from the pillow 10 to the reservoir 20. However, the series of valves 90 and 80 are positioned such that the deflation control pump 50 controls the amount of liquid and ability of liquid to pass through. The valves 90 and 80 are positioned directionally from the pillow 10 to the reservoir 20, such that liquid may flow from the pillow 10 to the reservoir 20, but not in reverse. However, in this case, for the deflation control pump 50 to pump fluid, the activation valve 40 must be held open. The valve 80 ensures that the pillow 10 does not deflate due to pressure induced flow through the deflation pump 50. Thus, the activation valve 40 controls the unwanted leakage of fluid from the pillow 10 into the reservoir 20.

The valves 80, 90, 100, 110, 120 can comprise duckbill valves. The duckbill valve can be manufactured from materials such as, elastomers, rubbery polymers, nylons, polyesters, PTFE, HDPE, PMMA, PVC, PP, PF, PC, and polyamides. In some embodiments, the elastomer is a silicone and the rubbery polymer is soft butyl, or hard butyl.

Figure 3:
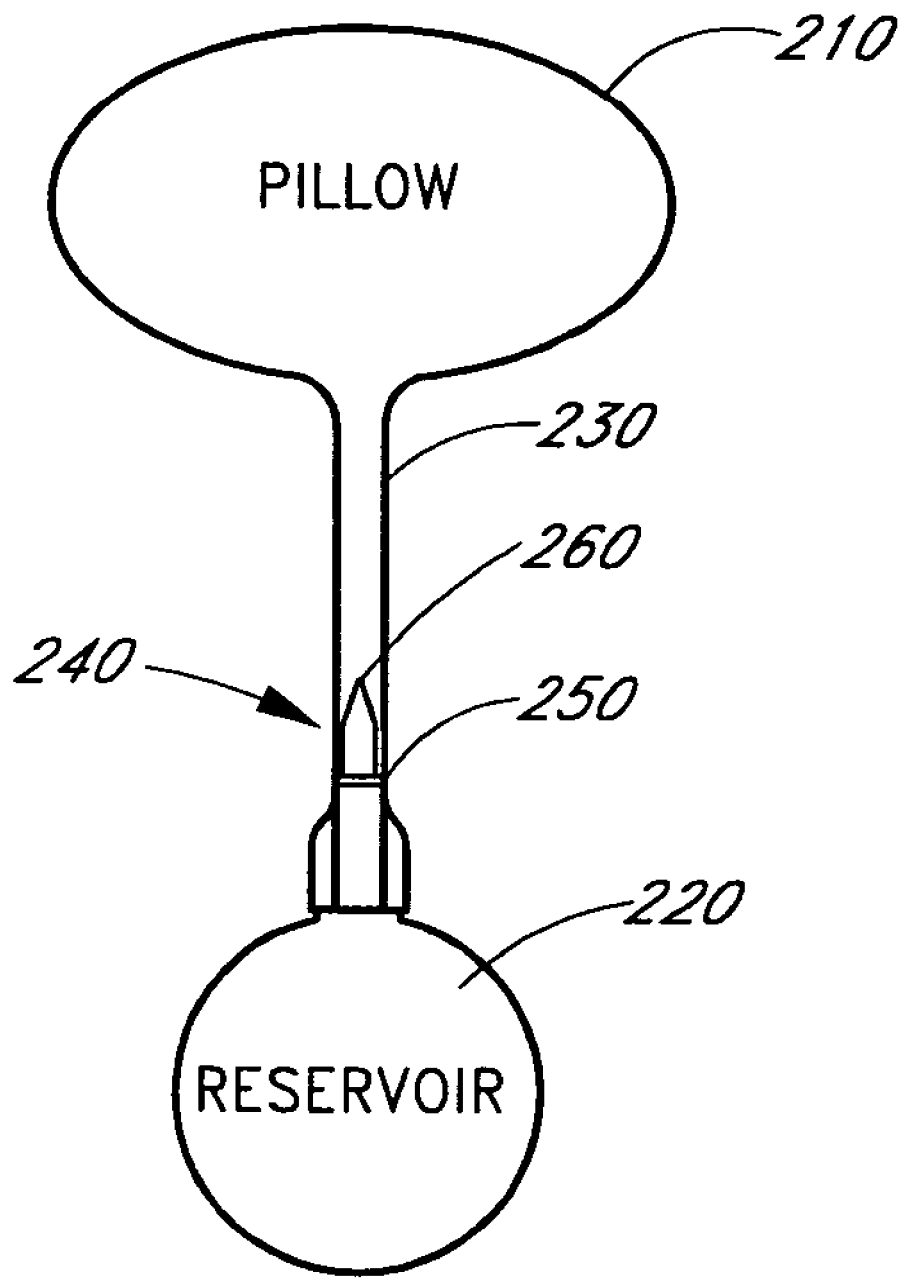
FIG. 3 is a front view of a urinary incontinence device of another preferred embodiment.
Figure 4:
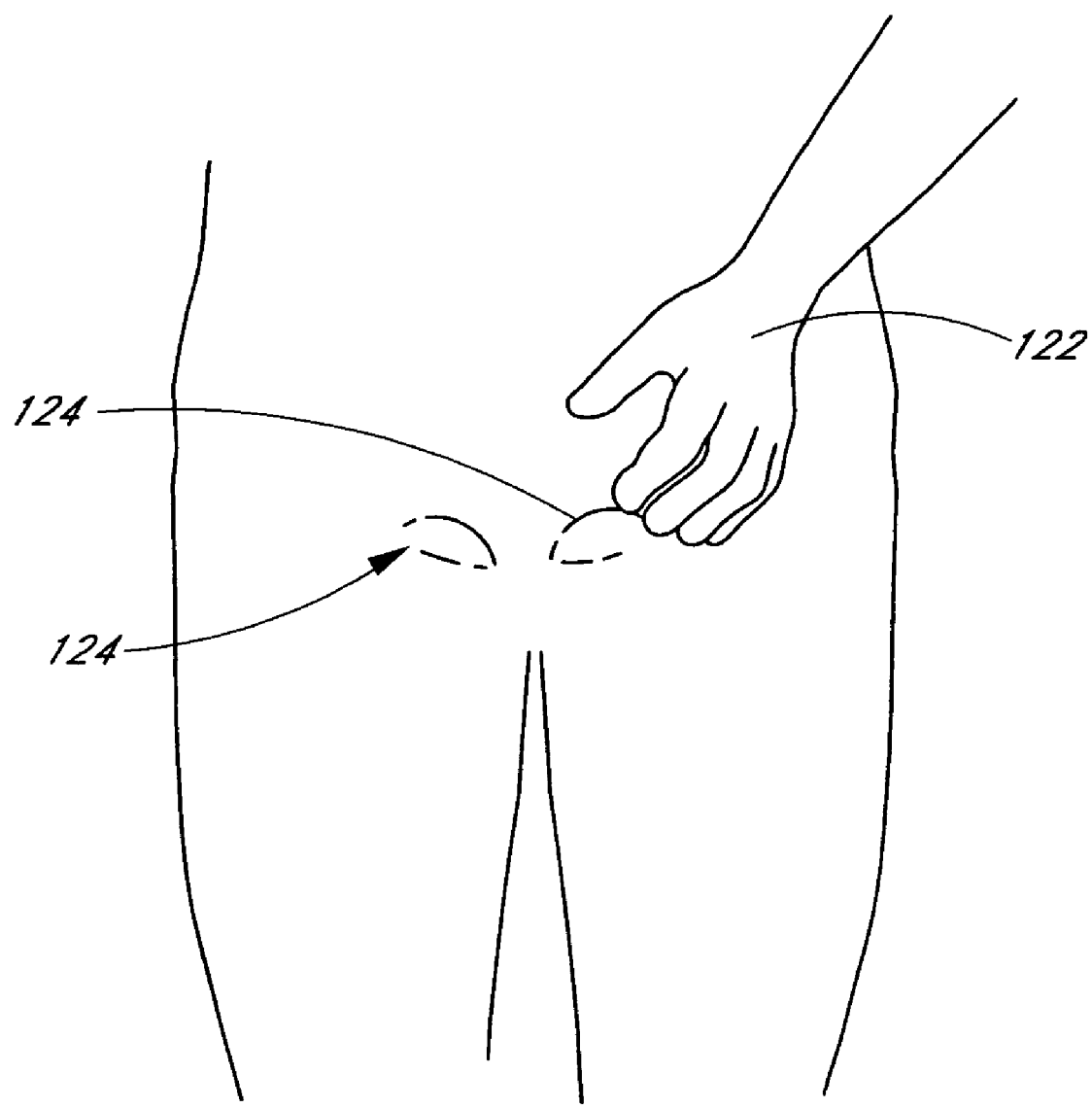
FIG. 4 is a perspective view of a patient adjusting the urinary incontinence device of FIG. 1.
Figure 5A:
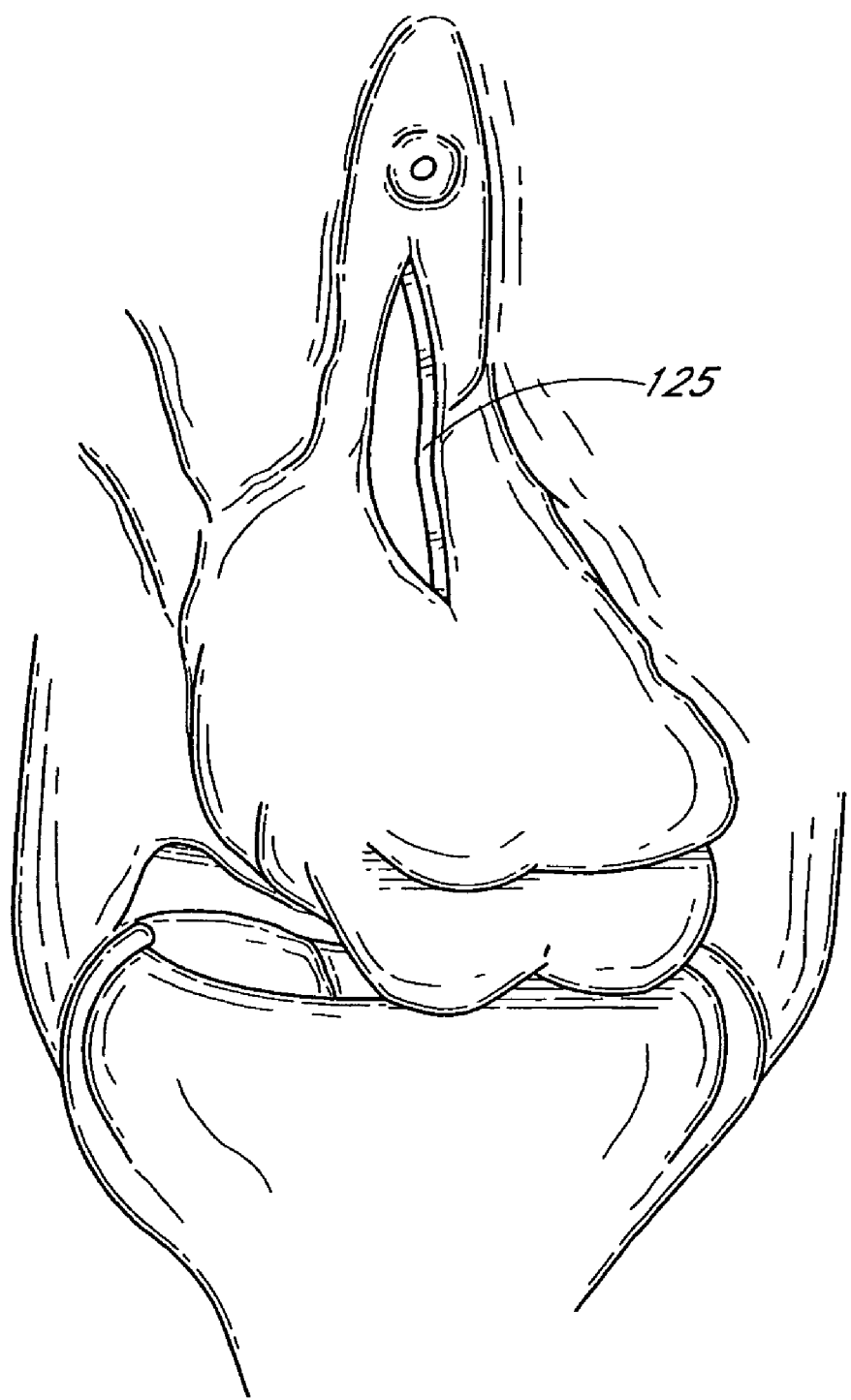
FIGS. 5A-C are views of the surgical procedure for implanting the AID of FIG. 1 into a female patient.
Figure 5B:
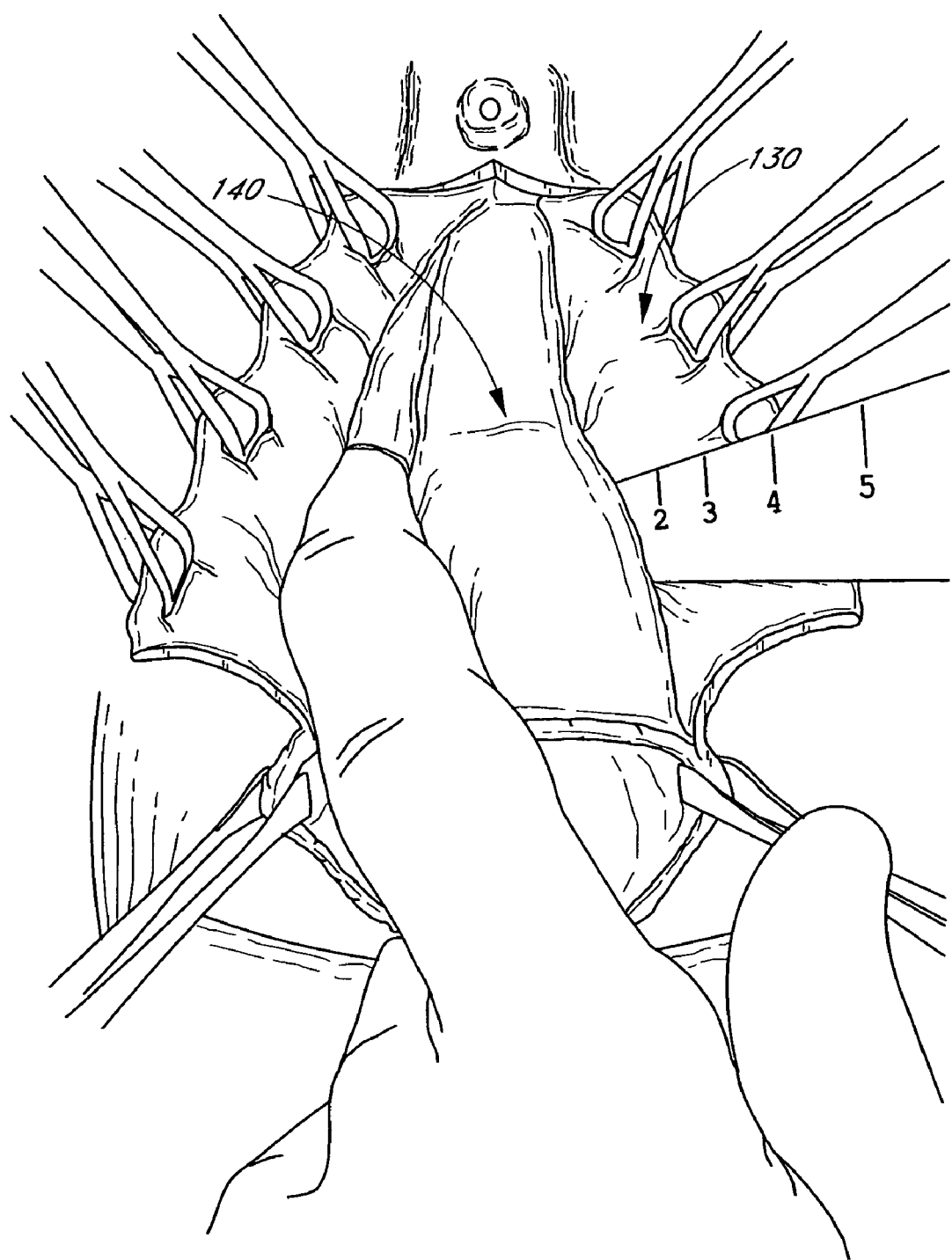
Figure 5C:
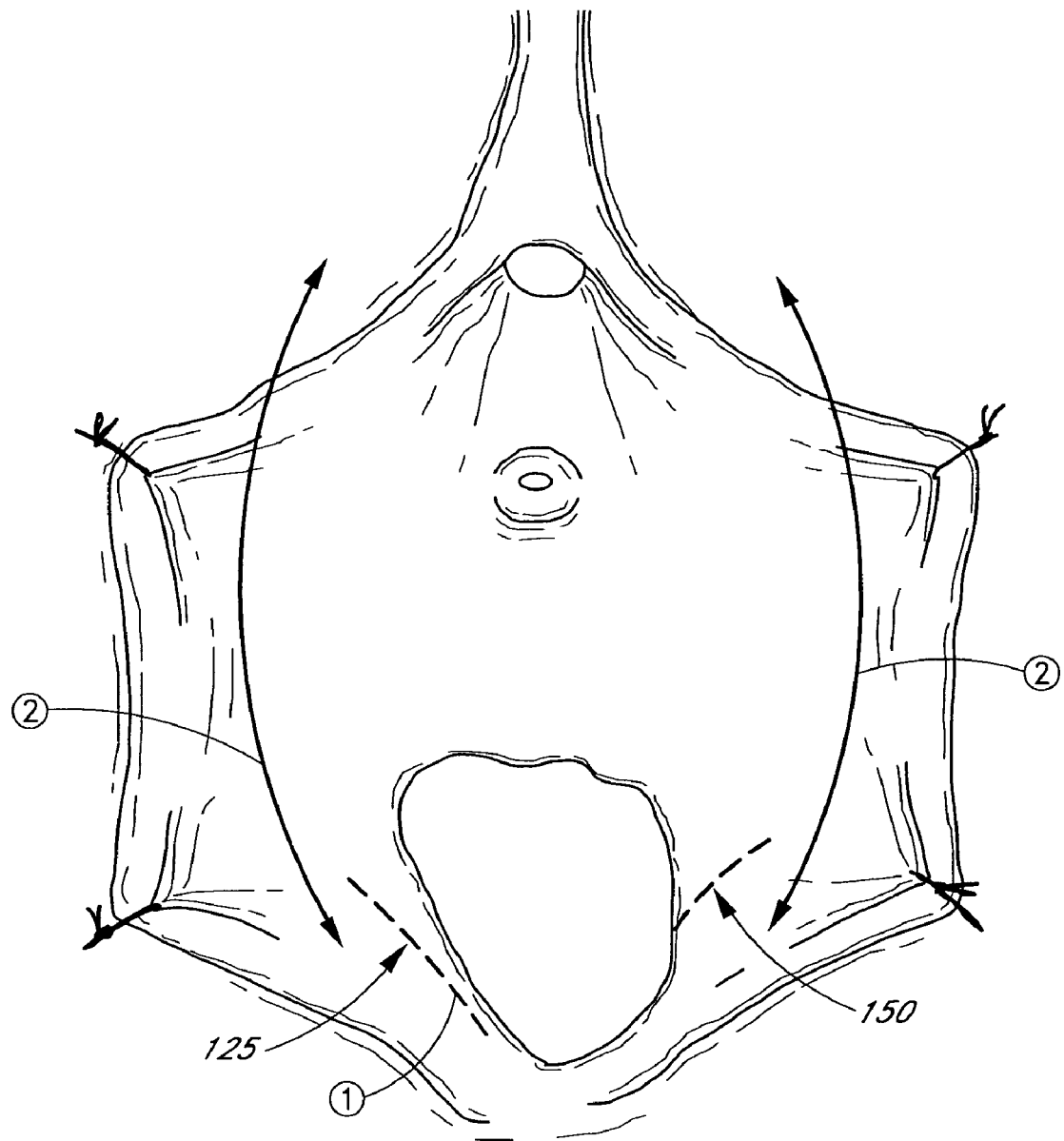

With reference to FIG. 3, the urinary incontinence device of a second preferred embodiment includes a pillow 210 and a reservoir 220 in fluid communication. The pillow 210 and reservoir 220 are connected by tubing 230, which provides both the inflation and deflation path. An activation valve 240 is provided between the reservoir 220 and pillow 210 at tubing 230. Activation valve 240, which can be a check valve, includes a rim 250 and an opening 260. Valve 240 and reservoir 220 can be located just beneath the skin of the patient. Valve 240 may be activated by pinching the valve.

The pillow 210 can be resilient and reservoir 220 may be non-resilient. The valve 240 permits fluid to flow out of the reservoir 220 while preventing fluid from leaving the pillow 210. Accordingly, by pinching valve 240 fluid escapes the pillow 210, thereby deflating pillow 210. By pressing reservoir 220, fluid flows through the value 240 from the reservoir 220 to pillow 210, thereby inflating pillow 210.

Alternatively, pillow 210 may be non-resilient and reservoir 220 may be resilient. In this embodiment, the reservoir 220 is similar to the self-inflating inflation and deflation bulb pumps of the first embodiment. By pressing the reservoir 220, fluid can be forced into the pillow 210, thereby inflating pillow 210. By simply pressing the valve 240, fluid can be sucked into the reservoir 220, thereby deflating pillow 210.

Figure 6:
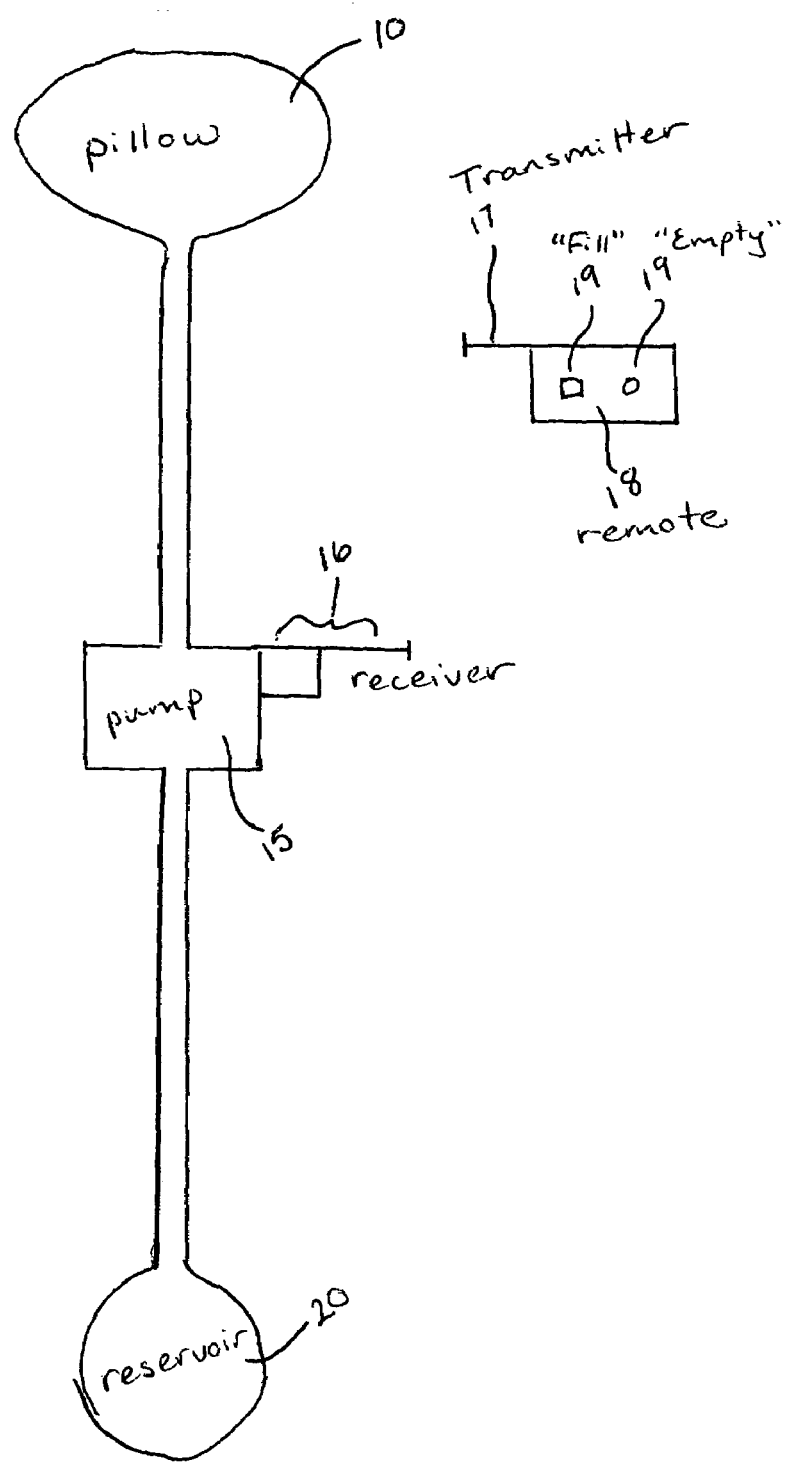
FIG. 6 is an embodiment of the urinary incontinence device that allows activation through a remote control device.

With reference to FIG. 6, an embodiment which works with a remote control is set out. The pillow 10 and reservoir 20 can be as set out in FIGS. 1-5. However, in this embodiment a pump 15 is included to move fluid from the pillow 10 to the reservoir 20. The pump may be any pump known to one of skill in the art and may operate by battery (for example lithium) or any other method of control. The pump 15 is attached to a receiver 16 which can send messages to the pump to pump fluid from the reservoir 20 into the pillow 10 (or vice versa). There my also be a valve or duckbill valve which stops fluid from moving back through the system. The system also has a transmitter 17 which may be part of a remote control device 18. The remote control device 18 may contain buttons 19 which allow the patient or user to send a signal to the pump to fill the pillow or to empty the pillow. The buttons 19 may be any device known to one of skill in the art which allows the patient to choose an action. Other embodiments of the button 19 include, but are not limited to, a switch, a compression, a knob, a roller, and a key. Further embodiments may allow the activation from a keyboard or computer device. Other embodiments may contain only one button 19 to "empty" the reservoir and when the system is in rest, the reservoir is filled. This can involve the use of a one-way valve which allows movement of fluid in only one direction.

Operation

The incontinence device works to help the normal sphincter muscles to close the sphincter. More particularly, the incontinence device allows for complete closure of the sphincter and may or may not help with the opening of the sphincter. With reference to FIG. 1, the pillow 10 is positioned under the urethra such that when filled, it helps to constrict the flow of urine through the urethra. If the patient wants to add liquid to the pillow 10, he or she pushes the self-expanding inflation control pump 30 on the left side of the diagram. The pressure caused by this motion causes a small amount of fluid to move through the tubing 60 from the reservoir 20 into the pillow 10, which then inflates more and constricts the urethra more. If the patient wants to remove fluid from the pillow 10, he or she pinches the activation valve 40 on the left side of the diagram by pushing on the side of the valve which he or she feels under the skin and by simultaneously pushing on the self-expanding deflation control pump 50 enough to open the associated check valve or valves. Then, with the activation valve 40 held open, he or she pushes on the self-expanding deflation control pump 50 and fluid moves from the pillow 10 into the reservoir 20, thus, reducing the pressure on the urethra. FIG. 3 shows a patient 122 adjusting the pillow (not shown) by pressing a bulb 124, located under the skin. Both of the bulbs 30, 50, and the activation valve 40 are similarly located just beneath the patient's skin.

Typically, it should only be necessary for the patient to adjust the pillow periodically. For example, after inflammation goes down and healing of the surgery, after a number of years of use, or due to any changes in regional anatomy and/or micturition physiology. Nevertheless, the patient will have the option of using the adjustability of the device for his/her daily urinary functions and to avoid incontinence or discomfort. For example, the patient may decide to err on the side of slight over-inflation during a public engagement. Alternatively, the patient may choose to void the bladder completely by under-inflating the pillow. In one embodiment, the patient may use the controls for daily urination. However, it is envisaged that this will not be necessary and that the patient may obtain natural urination control by choosing the correct inflation of the pillow.

Operative Techniques

The operative technique can be an office procedure which does not require an extensive stay in a hospital and may be an out-patient procedure. One example of such a procedure is detailed below. Preferably, the procedure is non-invasive and does not include incision of any major organs. However, it is envisioned that the surgeon may find that the patient's tissues are not in a state to hold the AID in position. Under these circumstances, the surgeon may decide to perform a slightly more invasive procedure somewhat like a TVT procedure as known to one of skill in the art.

One embodiment of the general procedure for a female is as follows:

Under the physician's/patient's choice of anesthesia, the patient is placed in a dorso lithotomy position and is prepped and draped in a sterile fashion. The bladder is catheterized and emptied. Methylene blue or sterile milk is given intravesically to assure notification of vesical entry. A midline incision 100, approximately 3-5 cm in length is made (see FIG. 4A). The vaginal mucosa 130 is dissected off and away from the pubocervical fascia 140 (see FIG. 4B). The AID is then placed at the urethrovesical to mid urethra. Small incisions 150 on the right and left labia (see FIG. 4C) will create an opening ① to a tunnel ② through which parts of the AID are threaded to each labial side for future patient adjustment The AID is placed such that the reservoir and one adjustment device are placed on one side and the other adjustment device is placed on the other side.

Depending on the patient's tissues, the surgeon may decide to insert the AID in the pubic area (somewhat like the TVT device). Alternatively, the surgeon may decide to use attachments and sutures to adjacent ligamentous tissues such as, but not limited to, Cooper's ligament, using different instruments such as a capioCL ™ device.

For implantation into a male patient, the device may be implanted such that the reservoir and one bulb are in one scrotum and the other bulb is in the other scrotum. Alternatively, as with the female, depending on the tissues, the surgeon may decide to insert it into the mons pubis.

Although the present invention has been described in terms of certain preferred embodiments, those skilled in the art will recognize that other and further changes and modifications may be made hereto without departing from the spirit of the invention, and it is intended to claim all such changes and modifications as fall within the true scope of the invention. Accordingly, the scope of the present invention is not to be limited by the particular embodiments described, but is to be defined only by reference to the appended claims and equivalents thereof.

What is claimed is:

1. A method of controlling urinary incontinence, comprising:
    providing a device comprising a pillow and a control element just under the skin, wherein said pillow is located adjacent the urethra;
    adjusting the pressure applied by said pillow to said urethra by activating said control element through the skin to selectively inhibit urination.

2. The method of claim 1, wherein said control element comprises a valve.

3. The method of claim 1, wherein said control element comprises a bulb.

4. The method of claim 1, wherein said control element comprises a pump.

5. The method of claim 1, wherein said control element comprises a one-way valve directed contrary to the flow direction.

6. The method of claim 1, wherein said control element comprises a series of valves.

7. The method of claim 1, wherein said control element is activatable by radiowaves, soundwaves, touch, pressure, or temperature.

8. The method device of claim 1, wherein said urinary incontinence device alleviates incontinence in the female bladder.

9. The method of claim 1, wherein said pillow is configured to rest at the junction of the bladder and the urethra.

10. The method of claim 1, wherein said pillow is implanted in conjunction to the bladder neck.

11. The device of claim 1, wherein said pillow is implanted in conjunction to the bladder.

12. A patient-adjustable urinary incontinence device comprising:
    a pillow, configured for implantation adjacent a patient's urethra;

a patient-adjustable valve for draining the pillow; and a patient-adjustable pump for filling the pillow to inhibit urination, wherein said pump comprises a series of valves and wherein said valve comprises a one-way valve directed contrary to the flow direction.

13. The device of claim 12, wherein said pump is just under the skin.

14. The device of claim 12, wherein said valve is just under the skin.

15. The device of claim 12, further comprising a remote control device.

16. The device of claim 12, wherein said pump is a reservoir.

17. The device of claim 12, wherein said pillow is resilient.

18. The device of claim 16, wherein said reservoir is resilient.

19. The device of claim 12, wherein said pump comprises a bulb.

20. The device of claim 12, wherein said pump comprises a series of valves.

* * * * *

UNITED STATES PATENT AND TRADEMARK OFFICE
CERTIFICATE OF CORRECTION

PATENT NO. : 7,608,067 B2  
APPLICATION NO. : 10/703287  
DATED : October 27, 2009  
INVENTOR(S) : Aram Bonni It is certified that error appears in the above-identified patent and that said Letters Patent is hereby corrected as shown below:

Column 12, Line 55, in claim 8, after "method" delete "device".

Column 62, in claim 11, change "device" to -- method --.

Signed and Sealed this

Sixteenth Day of March, 2010

David J. Kappos  
*Director of the United States Patent and Trademark Office*